United States Patent [19]

Broderick et al.

[11] Patent Number: 4,770,053
[45] Date of Patent: Sep. 13, 1988

[54] AUTOMATIC INDEXER ASSEMBLY

[75] Inventors: Daniel J. Broderick, Enfield; Michael T. Luedke, North Granby, both of Conn.

[73] Assignee: Combustion Engineering, Inc., Windsor, Conn.

[21] Appl. No.: 916,349

[22] Filed: Oct. 7, 1986

[51] Int. Cl.[4] .................. F28G 15/00; G01H 17/00
[52] U.S. Cl. .................. 73/866.5; 165/11.2; 414/750; 376/245
[58] Field of Search .............. 376/245, 249, 463, 260; 73/866.5, 623; 165/11.2, 11.1, 76; 414/146, 750, 749

[56] References Cited

U.S. PATENT DOCUMENTS

| | | | |
|---|---|---|---|
| 3,845,463 | 10/1974 | Timbs | 73/623 |
| 3,913,752 | 10/1975 | Ward et al. | 414/750 |
| 4,018,345 | 4/1977 | Formanek et al. | 414/750 |
| 4,177,676 | 12/1979 | Welker | 73/866.5 |
| 4,631,967 | 12/1986 | Welker | 73/866.5 |
| 4,633,713 | 1/1987 | Mesnard et al. | 73/866.5 |
| 4,638,667 | 1/1987 | Zimmer et al. | 165/11.1 |

Primary Examiner—Deborah L. Kyle
Assistant Examiner—Daniel Wasil
Attorney, Agent, or Firm—John H. Mulholland

[57] ABSTRACT

An automatic indexer assembly provides a constant axial and rotational movement of a signal-producing-sensor probe through a zone of a tube to be inspected with minimum signal distortion by means of threadedly connected fixed and movable hollow shafts. A probe tail is clamped to move with the movable shaft as it is driven by a constant speed drive motor and gear reducer mounted on a platform and guide plates which move with the movable shaft along a track parallel to the shaft axis. A water swivel and electrical slip ring also move on a platform with the movable shaft. Twisting of a fluid supply line and an electrical supply line is minimized. Constant sensor movement can be accomplished to permit accurate recording of the signal produced on a recording means with a minimum of backlash, acceleration, deceleration, or intermittent variables distorting the signal.

7 Claims, 5 Drawing Sheets

AUTOMATIC INDEXER ASSEMBLY

FIELD OF THE INVENTION

The present invention relates to an apparatus for the inspection of heat exchanger tubes and, in particular, the tubes of a nuclear steam generator after they have been in service in the production of electricity.

BACKGROUND OF THE INVENTION

It has previously been attempted to manually withdraw and rotate a signal-producing-sensor probe through a zone of a tube which is desired to be inspected and to visually note the probe position while recording the signal from such inspection for analysis. The inspection has been performed by manually rotating an internally threaded hollow shaft to react against an externally threaded hollow shaft concentrically assembled therein. A probe tail including electrical and fluid supply lines extends through, and is clamped to, the internally threaded shaft, for rotation therewith. Since the probe and its tail are torsionally rigid, the rotation imparted to the probe tail, rotates the probe and twists the electrical and fluid supply lines. Because of the twisting, the rotation and the withdrawal motion must be periodically interrupted to manually untwist the supply lines. The inspection is thus interrupted. Moreover, because of the interruptions and manual rotation irregularities, backlash in the system creates acceleration, deceleration and other intermittent variables which may distort the signal to be recorded. This is especially so if the tube produces a variable resistance to rotation of the probe due to variations in friction, surface cleanliness, flaws and interruptions. For these reasons, these manual attempts have not been successful in providing a constant and reliable signal.

Accordingly, there has been a need in the art for an automatic indexer assembly which provides a constant axial and rotational movement of a signal-producing-sensor probe through a zone of a tube to be inspected and recorded for analysis.

SUMMARY OF THE INVENTION

The present invention provides an automatic indexer assembly for constant rate withdrawal and rotation of a tube inspection signal-producing-sensor probe having a torsionally rigid flexible tail containing electrical and fluid supply lines. The automatic indexer assembly permits accurate recording of the signal produced on a recording means with a minimum of backlash, acceleration, deceleration or intermittent variables distorting the signal.

The indexer assembly includes a telescopingly assembled and threadedly connected axially fixed hollow shaft and axially movable hollow shaft. The latter has a clamp means securing the probe tail within the hollow shafts for movement with the axially movable hollow shaft. Torsional rigidity of the probe tail creates rotary motion of the probe within a tube to be inspected as it is withdrawn under control of the constant rotation of the axially movable shaft along the threads of the axially fixed shaft.

The axially movable shaft is rotationally driven at a constant rate by means of a chain sprocket on its exterior drivingly connected to a motor mounted on a fixed track for movement in concert with the axially movable shaft parallel to the axis of the hollow shafts.

A slip ring connects to the electrical supply line of the probe tail to provide a means for minimizing twisting of the electrical supply line while maintaining contact with a fixed electrical supply line.

A fluid swivel connects to the fluid supply line of the probe tail to provide a means for minimizing twisting of the fluid supply line while maintaining fluid communication with a fixed fluid supply.

The automatic indexer assembly includes an encoder attached to the motor which senses and records rotations and degrees of rotations. This input in connection with the signal input from the probe produces an accurate flaw location indication on a recording chart.

It will be seen that with lead-screw accuracy in one constant withdrawal motion utilizing the motor-produced constant rotation, the recorded signal will be highly accurate with virtually no backlash, acceleration or deceleration distortion.

DETAILED DESCRIPTION OF THE PREFERRED EMBODIMENT

Figure 1:
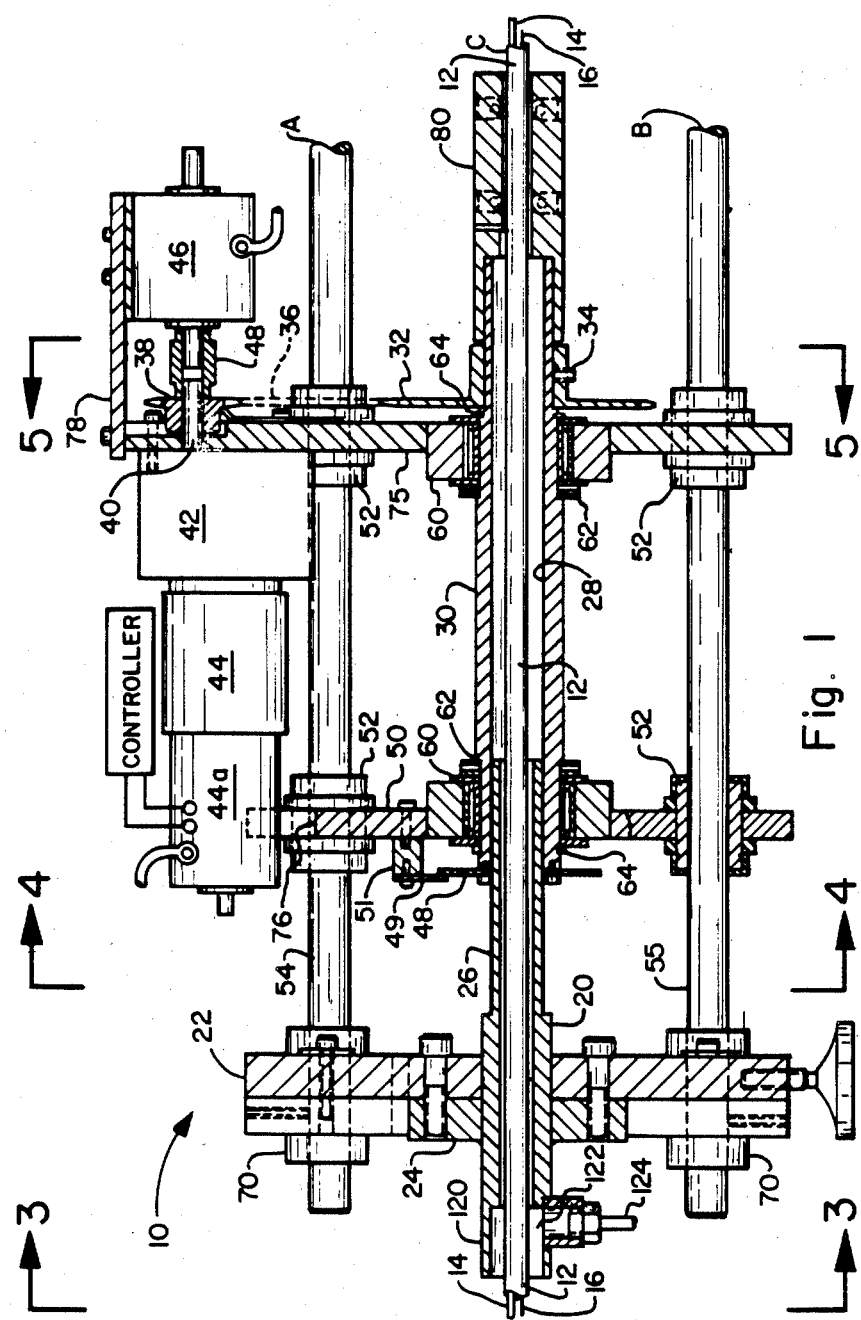
FIG. 1 is a cross-sectional elevation view of the automatic indexer assembly end portion closest to a tube to be inspected, with some elements shown in cross-section and some in full, for purposes of clarity.

Like elements are assigned like numbers in the various views of the drawings.

The automatic indexer assembly for constant rate withdrawal and rotation of a tube inspection signal-producing-sensor probe according to the principles of the invention is generally designated by the numeral 10. The torsionally rigid flexible tail of a tube inspection signal-producing-sensor probe is indicated by the numeral 12 and includes a fluid line 14 and an electrical conductor 16. A tubular plastic sheath makes up the outer covering of the tail 2 of the probe (not shown).

The inspection probe typically will be of the ultrasonic type which is well-known in the art as comprising a tapered head and O rings for fitting within the tube of a nuclear steam generator, for example, which is to be inspected. The fluid supplied by the line 14 acts as an ultrasonic couplant and the conductor communicates the signal of a transducer in the probe head.

The automatic indexer assembly 10 includes an axially and rotationally fixed hollow shaft 20 mounted within a central opening of a front end plate 22 by means of an annular flange 24 welded to the shaft and bolted to the front plate.

The inner end of the fixed shaft 20 and most of its length is threaded on its exterior with thread means 26. Telescopingly received on the end of the fixed shaft 20, by means of internal threads 28, is rotatable and axially movable hollow shaft 30. A drive sprocket 32 is attached by means of a set screw 34 to the exterior of the hollow shaft 30. The sprocket 32 is driven by a chain 36 from a smaller sprocket 38. The sprocket 38 is driven by an output shaft 40 from a gear reducer 42 mounted with an electrical motor 44 as a unit. Such a unit may be obtained from Electro-Craft Corporation of Hopkins, Minn., and is known as their Series E-586 MGHP. A motor controller from the same source is part of the package and is designated E-586-M. Upon activation, the controller provides the required revolution rate of the rotating hollow shaft. Typically, the rotation and withdrawal is accomplished by providing a uniformly threaded connection of twenty pitch between the fixed hollow shaft 20 and the rotating and axially movable hollow shaft 30. Accordingly, for every 1/20th of an inch withdrawal, the probe rotates one full turn.

An encoder 46 is tied to the drive shaft 40 by means of a coupler 48. The encoder transmits a signal which may be set so that for every rotation of the encoder shafts signal in the form of 600 pulses is sent which equals 360 degrees of rotation of the driven shaft 30. The encoder 46 may be obtained from Durant, a division of Eaton Corporation located in Watertown, Wis., and is designated Durant Encoder Number 39702. For convenience of recording, a Durant Series 5882 communications converter is used in connection with the encoder to convert the 600 pulses representing a revolution of the encoder into 360 degrees of drive shaft travel along the twenty pitch thread. The output from the communications converter can be fed to a strip chart recording device for analysis. Suitable electrical connections are made to the various electrical components by flexible electrical conduits being attached to exterior connection points.

The end of the rotating hollow shaft 30 has an angular degree indicator dial 48 mounted thereon for visual indication of the shaft position. This is a matter of convenience to the operator in using the equipment and is made easier by a wire pointing device 49 mounted on a guide plate 50 by means of a suitable mounting block 51.

The guide plate 50 has linear bearings 52 adjacent each of its four corners to support it on each of four shafts, 54, 55, 56 and 57. The shafts 54, 55, 56 and 57 define a track means along which the guide plate 50 slides as it is driven by the hollow axially movable and rotatable shaft 30. The guide plate 50 has a central opening with a needle bearing assembly generally designated by the numeral 60 fixed to the shaft 30 such that the shaft 30 is supported by, and freely rotates within, the opening of the guide plate 50. A shoulder 62 and securing ring 64 insure that the guide plate 50 and the shaft 30 move together in an axial direction along the guide shafts 54, 55, 56 and 57 which make up the track means. The ends of the shafts 54, 55, 56 and 57 of the track means are secured in collars 70 at the corners of the front end plate 22 and similar end plate 72 at the opposite end of the indexer assembly. The end plates 22 and 72 are mounted on suitable leveling pads 74.

A motor mount guide plate 75 supports the end of the movable hollow shaft 30 opposite guide plate 50 and adjacent to drive sprocket 32 on the shaft exterior. The guide plate 75 has a needle bearing assembly 60 and retaining devices 62 and 64 which function in the same manner as they do relative to the guide plate 50. The motor mount guide plate 75 also has linear bearings 52 at its four corners for movement along the shafts 54, 55, 56 and 57 of the track means. The motor 44 and the gear reducer 42 are suitably mounted, as by means of bolts, on the upper portion of the motor mount guide plate 75 for movement therewith. A cutout 76 is provided in the guide plate 50 for accommodation of the forward end 44a of the motor 44. A horizontal mounting plate 78 is secured as, for instance, by bolting, to the top of the motor mounting guide plate 75 to act as a support of encoder 46. Thus, it will be seen that the motor and gear reducer assembly as well as the encoder all move together with their appropriate drive output means in concert with the movable shaft 30 as it slides along the threaded connection with the fixed hollow shaft 20.

Fixedly mounted for travel with the movable hollow shaft 30 on the end of the shaft, is a clamp means 80 which clamps and holds the probe tail 12 for motion with the shaft 30 during its constant rotation and withdrawal movement along the 20 pitch threads of the connection with the fixed shaft 20. It is this movement that brings the probe head at a constant rate of withdrawal and rotation through the zone of the tube to be inspected in a manner which, because of the accurate and constantly controlled drive of the motor 44 as directed by the controller, permits an accurate recording of the scanning signal produced in the probe transducer.

The motor, gear reducer and controller, when taken in combination, make up a drive system which is marketed by Electro-Craft under the trademark MOTOMATIC. This drive system consists of two basic units, a permanent magnet DC motor-generator and a solid state electronic controller. The motor-generator has two armatures on the same shaft - one to drive the motor shaft and the other to generate voltage proportional to speed. The signal from the generator is fed to the controller where it is compared with a speed command voltage. The controller provides more or less voltage to the motor winding in order to increase or decrease the speed to maintain a balance between the speed command voltage and the generator voltage. A pre-set and regulated constant speed is thus insured regardless of changes in load or line voltage.

Because the probe tail 12 is clamped to the axially and rotationally movable hollow shaft 30, it rotates and withdraws with the shaft as it progresses along its threaded connection with fixed shaft 20. Therefore, unless adequate means are provided, the probe tail 12 and its fluid supply line 14 and electrical conductor 16 will become tangled and require interruption of the inspection withdrawal through the zone of the tube by the probe head. Accordingly, a platform 82 is mounted on the track means shafts 55 and 56 on linear bearings 52 to support and guide both a water swivel 84 and an electrical slip ring assembly 86.

The probe tail 12 is clamped, by means of a clamp structure 88 similar to clamp structure 80, to a rotating shaft 90 of the water swivel 84. The rotating shaft 90 in the area of the clamp portion 88 has a single passageway which branches into a pair of passageways. The first branch is an axial passageway 92 through which the conductor 16 passes and which extends entirely through the water swivel structure 84 and its rotating shaft 90 The second branch is an eccentric passage 94 which is in fluid communication with the fluid conducting supply line 14. The water swivel shaft 90 is driven by the tortionally rigid probe tail 12 through the clamp 88. As the shaft 90 turns, a port 96 transverse to the passageway 94 and in communication therewith opens into an annular chamber 98 in the fixed housing of water swivel 84. The housing of water swivel 84 is mounted by means of a hinged clamping block 100 on the movable platform 82. The clamping block 100 includes a hinge 102 for access to an annular opening for the annular water swivel 84 by pivoting of the top half of the clamping block 100 around the hinge 102. Water from a fixed supply line 104 thus passes through annular chamber 98 of the fixed structure of water swivel 84 to the rotating transverse port 96 of rotating shaft 90 during operation of the automatic indexer.

From the passageway 94 the water enters the water supply line 14 for passage to the probe via the length of the probe tail 12. The rotating shaft 90 is suitably sealed in the fixed water swivel or rotary union 84 by means of O-rings 106 on either side of the annular passageway 98.

A suitable water swivel or rotary union for use in the invention is the Deublin model 21-081-101 manufactured by the Deublin Company of Northbrook, Ill. The Deublin rotating water swivel is modified by extending the passageway 92 throughout the length of the shaft 90 and providing it with a tube 108 for lining the passageway and extending beyond the end of the shaft 90 opposite clamping cap 88. The tube 108 contains the electrical conductor 16 and permits it to be extended axially outwardly for connection to the rotor 110 of the slip ring assembly 86. The shaft 90, a coupling member 112 and the electrical slip ring rotor 110 all rotate together because of a coupling sleeve 114 which unites them for this purpose by means of suitable set screws, or equivalent, 115.

Figure 2:
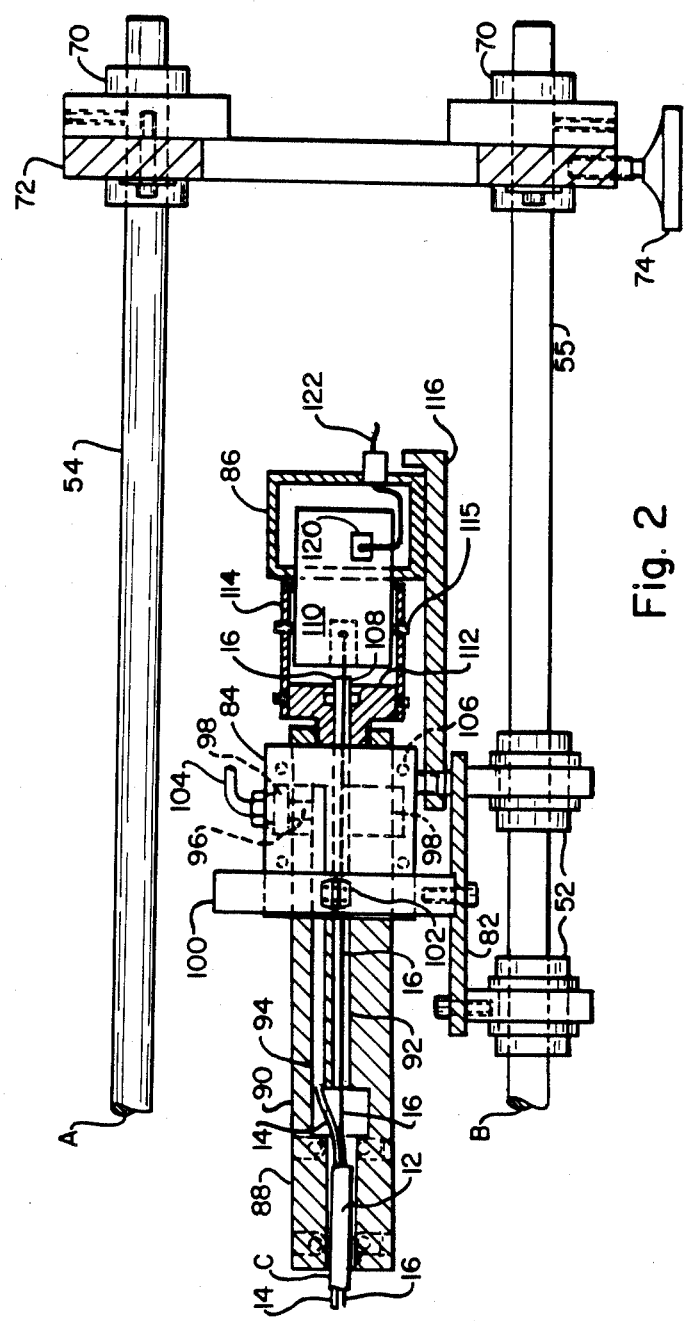
FIG. 2 is a cross-sectional elevation view similar to FIG. 1 showing the end portion opposite to the end portion of FIG. 1. The common apparatus points of FIGS. 1 and 2 are indicated at locations A and B and the probe tail common points at location C.
Figure 3:
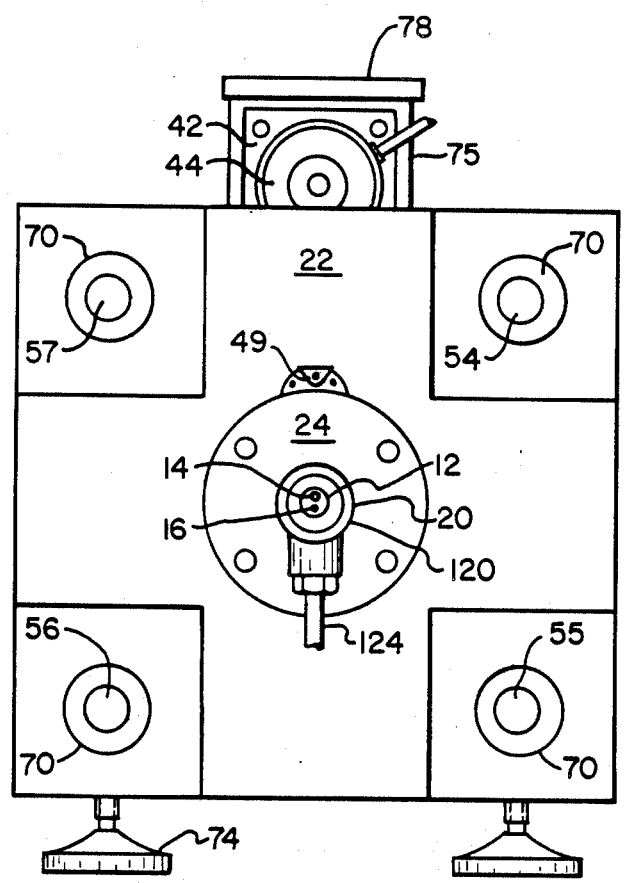
FIG. 3 is an end elevation view taken along the line 3—3 of FIG. 1.
Figure 4:
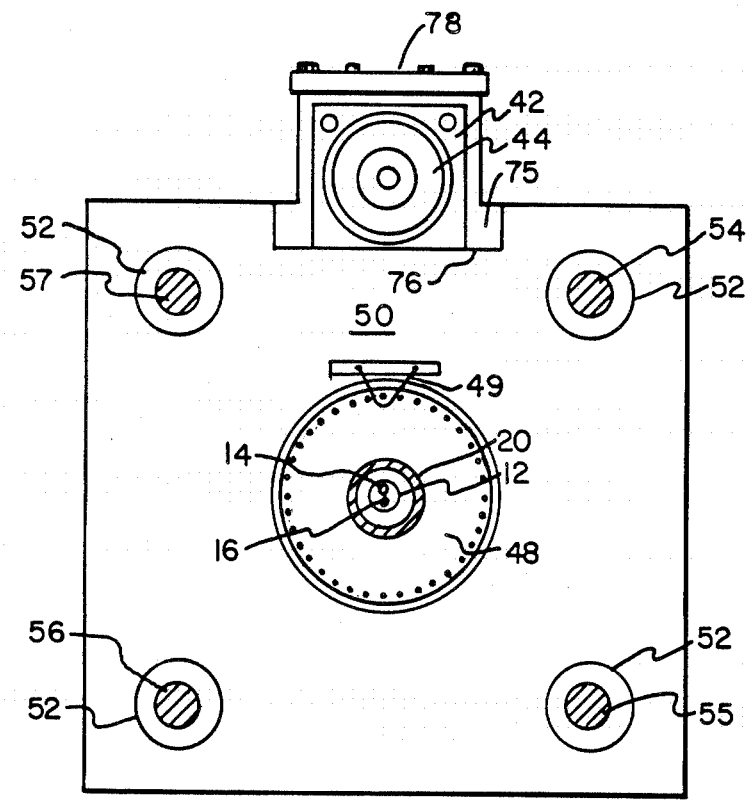
FIG. 4 is a cross-sectional elevation view taken along the line 4—4 of FIG. 1.
Figure 5:
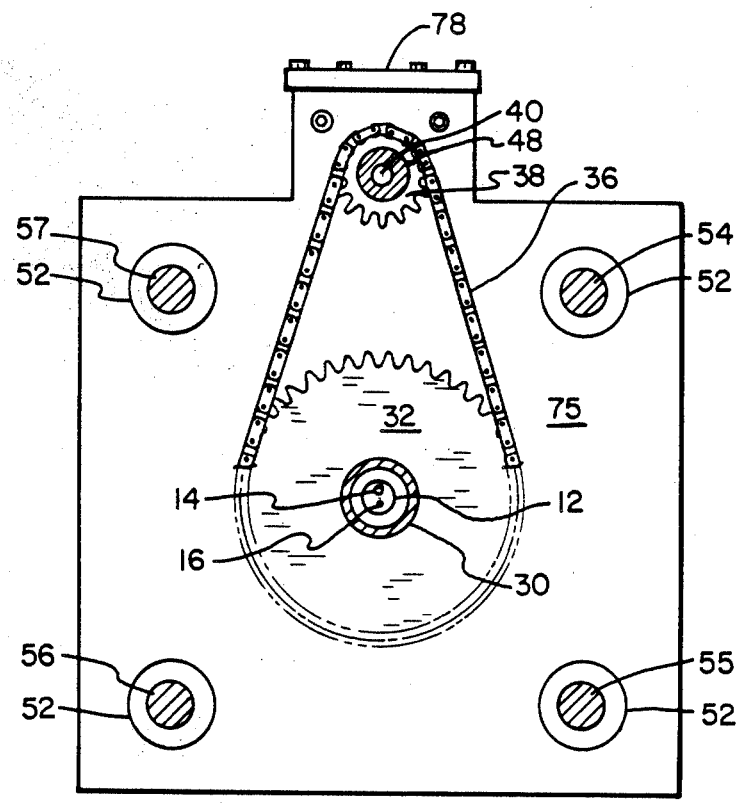
FIG. 5 is a cross-sectional elevation view taken along the line 5—5 of FIG. 1 in the direction opposite to FIGS. 3 and 4, with certain parts schematically shown for clarity.

The slip ring 86 is shown schematically in FIG. 2 and is mounted on a platform 116 bolted to and extending from the platform 82. Electrical contact through the slip ring assembly from the rotor 110 is made by means of a brush 120 with suitable external connections 122 to a fixed power supply connection through a flexible cord. Thus it will be seen that the platforms 82 and 116 carrying the water swivel and slip ring move with the hollow axially and rotationally movable shaft 30 along the track means formed by shafts 55 and 56.

When connected to the probe, the automatic indexer assembly 10 is also connected at its exposed end of fixed hollow shaft 20, on the surface 120, to a probe guide tube (not shown). The typical guide tube is a flexible sheath running to the tube to be inspected and suitably aligned therewith. Water which has been communicated to the probe through the fluid supply line 14 of the probe tail 12 will exit along the guide tube inside and the probe tail outside until it reaches the hollow shaft 20 internal end cavity 122, where it will be drained through tube 124.

Thus, it will be seen that an automatic indexer assembly 10, which is particularly useful for ultrasonic probes which use water as a couplant, has been provided, whereby a constant axial and rotational movement of the probe through a zone of a tube to be inspected can be accomplished to permit accurate recording of the signal produced on recording means with a minimum distortion from backlash acceleration, deceleration or intermittent variables distorting the signal. The undistorted signal may thus be analyzed for an accurate determination of the interior condition of the inspected tube.

We claim:

1. An automatic indexer assembly for constant rate withdrawal and rotation of a tube inspection signal-producing-sensor probe having a torsionally rigid flexible tail containing electrical and fluid supply lines, said indexer assembly comprising:
   an axially fixed hollow shaft;
   an axially movable hollow shaft telescopingly connected to said fixed hollow shaft;
   means for securing the probe within said axially movable hollow shaft for movement therewith;
   means threadedly connecting said axially fixed hollow shaft and said axially movable hollow shaft;
   means fur rotationally driving one of said shafts at a constant rate of rotation thereby to axially move said probe and said axially movable shaft;
   means for minimizing twisting of said electrical supply line moving with said probe and electrically connecting said electrical supply line to a non-rotating electrical supply line;
   means for minimizing twisting of said fluid supply line moving with said probe and fluidly connecting said fluid supply line to a non-rotating fluid supply line;
   whereby, a constant axial and rotational movement of said signal-producing-sensor probe through a zone of a tube to be inspected can be accomplished to permit accurate recording of the signal produced on a recording means with a minimum of backlash, acceleration, deceleration or intermittent variables distorting the signal.

2. The automatic indexer assembly of claim 1 in which the axially movable hollow shaft is drivingly connected to the means for rotationally driving one of the hollow shafts.

3. The automatic indexer assembly of claim 1 in which the axially movable hollow shaft has the means threadedly connecting it to the axially fixed hollow shaft located on its interior and has the means for rotationally driving one of the hollow shafts drivingly connected to its exterior.

4. The automatic indexer assembly of claim 3 in which the means for rotationally driving one of the hollow shafts includes a motor mounted for movement along track means parallel to the axis of said hollow shafts.

5. The automatic indexer of claim 4 in which the means for rotationally driving includes a sprocket driven by said motor and mounted on the exterior of said axially movably mounted shaft such that said motor and said sprocket move together parallel to the axis of said hollow shafts.

6. The automatic indexer assembly of claim 1 in which means for sensing and signalling rotational position of the probe to a recording means are included.

7. The automatic indexer assembly of claim 5 in which the means for sensing and signalling rotational position of the probe to a recording means are mounted to move with the motor.

* * * * *